(12) United States Patent
Nielsen et al.

(10) Patent No.: US 8,173,427 B2
(45) Date of Patent: May 8, 2012

(54) METHOD OF PRODUCING A POPULATION OF POST-MITOTIC CELLS OF THE NEUTROPHIL LINEAGE

(75) Inventors: Lars K. Nielsen, St. Lucia (AU); Emma L. Palfreyman, Fig Tree Pocket (AU); Nicholas E. Timmins, St. Lucia (AU)

(73) Assignee: The University of Queensland, Brisbane (AU)

( * ) Notice: Subject to any disclaimer, the term of this patent is extended or adjusted under 35 U.S.C. 154(b) by 14 days.

(21) Appl. No.: 12/375,098

(22) PCT Filed: Jul. 23, 2007

(86) PCT No.: PCT/AU2007/001019
§ 371 (c)(1),
(2), (4) Date: Feb. 26, 2010

(87) PCT Pub. No.: WO2008/011664
PCT Pub. Date: Jan. 31, 2008

(65) Prior Publication Data
US 2010/0151569 A1   Jun. 17, 2010

Related U.S. Application Data

(60) Provisional application No. 60/832,854, filed on Jul. 24, 2006.

(51) Int. Cl.
*C12N 5/00* (2006.01)
*C12N 5/02* (2006.01)
*C12N 5/071* (2006.01)

(52) U.S. Cl. ........ 435/377; 435/325; 435/372; 435/373; 435/375; 435/383; 435/384; 435/385

(58) Field of Classification Search .................. None
See application file for complete search history.

(56) References Cited

OTHER PUBLICATIONS

Sawai et al. (1999) Neutrophilic cell production by combination of stem cell factor and thrombopoietin from CD34+ cord blood cells in long-term serum-deprived liquid culture. Blood 93(2): 509-518.*
Dang et al. (2004) Controlled, scalable embryonic stem cell differentiation culture. Stem Cells 22(3): 275-282.*
De Leon et al. (1998) Design, characterization and application of a minibioreactor for the culture of human hematopoietic cells under controlled conditions. Cytotechnology 28: 127-138.*
Makino et al. (1997) Ex vivo culture of peripheral blood CD34+ cells: Effects of hematopoietic growth factors on production of neutrophilic precursors. J. of Hematotherapy 6: 475-489.*
Culpitt, SV (2001) Neutrophils: Collection, Separation, and Activation. Methods in Molecular Medicine 56: 177-189.*
Lichtenberger et al. (1999) A novel high-purity isolation method for human peripheral blood neutrophils permitting polymerase chain reaction-based mRNA studies. Journal of Immunological Methods 227: 75-84.*
Yokoyama et al. (2009) Derivation of functional mature neutrophils from human embryonic stem cells. Blood 113(26): 6584-6592.*

* cited by examiner

*Primary Examiner* — Anne-Marie Falk
(74) *Attorney, Agent, or Firm* — Edwards Wildman Palmer LLP

(57) ABSTRACT

A method is provided for producing a population of post-mitotic cells of the neutrophil lineage, which method comprises the ex vivo steps of: (a) providing a population of cells comprising neutrophil progenitor cells; and (b) culturing the population of cells in an animal cell culture medium comprising (i) one or more early acting cytokines and (ii) one or more cytokines that differentiate said progenitor cells into a neutrophil specific lineage, under conditions of low oxidative stress, the culture medium being agitated when the cells are at a cell density at which oxygen transfer via the surface of the culture medium is insufficient for growth of the progenitor cells and the progeny thereof under static conditions, to produce a population of post-mitotic cells of the neutrophil lineage. The resulting population of cells can be used to increase the number of neutrophils in a patient.

12 Claims, No Drawings

METHOD OF PRODUCING A POPULATION OF POST-MITOTIC CELLS OF THE NEUTROPHIL LINEAGE

FIELD OF THE INVENTION

The present invention relates to pharmaceutical compositions comprising non-activated neutrophils and methods of producing such compositions.

BACKGROUND TO THE INVENTION

Neutropenia is a blood disorder characterised by an abnormally low number of neutrophil granulocytes. Neutrophils are active phagocytes (engulfers). Being highly motile, neutrophils quickly congregate at a focus of infection or inflammation. Neutrophils usually make up 50-70% of circulating white blood cells and serve as the primary defense against infections by destroying pathogens. Hence, patients with neutropenia are more susceptible to infections and without prompt medical attention, the condition may become life-threatening. Neutropenia can be acute or chronic depending on the duration of the illness.

The spectrum of neutropenia related infections has shifted in the past 20 years with fungal infections, particularly invasive moulds such as *Aspergillus, Fusarium*, and *Zygomyces* emerging as the principal infectious cause of mortality and morbidity. The incidence of invasive *Aspergillus* infection in patients undergoing allogeneic bone marrow transplantation (BMT) is approximately 15 percent, with mortality rates of 30 to 80 percent. *Fusarium* infection in these patients is fatal in 70 percent of cases.

In order to better understand the problems presented by neutropenia, it is helpful to understand some basic principles about blood cells, including their source and their development.

Blood cells develop from multipotent stem cells. These stem cells have the capacity to proliferate and differentiate. Proliferation maintains the stem cell population, whereas differentiation results in the formation of various types of mature blood cells that are grouped into one of the three major blood cell lineages, the lymphoid, erythroid and myeloid. It is the myeloid lineage, which is comprised of monocytes (macrophages), granulocytes (including neutrophils), and megakaryocytes, monitors the bloodstream for antigens, scavenges antigens from the bloodstream, fights off infectious agents, and produces platelets, which are involved in blood clotting.

Neutrophils differentiate from haematopoietic stem cells through a series of intermediate precursor cells, which can be distinguished by their microscopic morphological appearance, including such characteristics as the size of their nuclei, cell size, nuclear/cytoplasmic ratio, presence/absence of granules, and staining characteristics (See *Atlas of Blood Cells: Function and Pathology*, second edition, Zucker-Franklin et al.) Initially, the multipotent stem cell, gives rise to myeloid "progenitor cells" that generate precursors for all myeloid cell lines. The first myeloid progenitor is designated CFU-GEMM for "colony forming unit—granulocyte, erythroid, macrophage and megakaryocyte". The CFU-GEMM progenitor, in turn, will give rise to a CFU-GM progenitor cell, which is otherwise known as a "colony forming unit—granulocyte macrophage". In all of these descriptive terms, "colony" generally refers to a cell that is capable of giving rise to more than 50 cells as measured in 14 day in vitro assays for clonal growth. These cells will divide at least six times.

The CFU-GM is a committed progenitor: —it is committed to differentiation into granulocytes and macrophages only. It is neither capable of differentiating into other types of cells nor is it capable of dedifferentiating into earlier stage progenitor cells. The CFU-GM progenitor cell may then differentiate into a myeloblast. The time required for differentiation from a CFU-GEMM to a myeloblast is believed to be about 1-4 days. A myeloblast is the first of the series of cells that may be referred to as "precursors" to the neutrophils, as such cells, once allowed to fully develop (differentiate), can only form neutrophils, which it is believed, are only capable of undergoing fewer than six cell divisions and, therefore, do not form colonies in in vitro assays as described previously.

Once differentiation has progressed to the myeloblast stage, the myeloblasts undergo terminal differentiation. Myeloblasts differentiate into promyelocytes, which, in turn, differentiate into myelocytes over a course of about 4-6 days. Within another 5 days or so, myelocytes differentiate into metamyelocytes, which, in turn, differentiate into banded neutrophils. These banded neutrophils finally differentiate into mature, segmented neutrophils, which have a half-life of about 0.3 to 2 days.

During this progressive, morphological differentiation, changes in the surface antigens of these cells can be observed. Further, as neutrophil precursor cells differentiate, they lose their capacity to proliferate. In general, the less mature neutrophil precursor cells, namely the myeloblasts, promyelocytes, and myelocytes, retain their ability to proliferate. However, the more mature neutrophils, namely the metamyelocytes and the banded neutrophils, lose their capacity to proliferate, although they continue to differentiate into mature, segmented neutrophils.

The current treatment for chemotherapy induced neutropenia varies, but it typically involves dosage modulation or the cessation of the cytotoxic therapy along with the administration of granulocyte-colony stimulating factor (G-CSF) or other stimulating factors to increase the circulating neutrophil count. Peripheral blood contains approximately 10% of the body's neutrophil pool. Agents such as G-CSF act by causing the near immediate release of stored mature neutrophils and an increase in renewal and differentiation of stored progenitor and precursor neutrophils. It then takes the bone marrow around 10-15 days to replenish the neutrophil stores and thus the levels of circulating neutrophils, an effort made more difficult with myeloablative therapy which tends to destroy the progenitor and precursor cells. Therefore, even with the administration of G-CSF, patients are likely to benefit from supplemental neutrophil transfusion.

U.S. Pat. No. 6,146,623 describes a technique that several companies have tried or are trying in order to develop stem cell progenitor or precursor based therapies for the treatment of neutropenia. This involves isolating haematopoietic stem cells, expanding these cells ex vivo to a point where they are of a committed lineage, but are not fully differentiated, and then transfusing the expanded cells into the patient. An emphasis has been put on an expansion that produces cells that are predominantly late progenitors and precursors of mitotic neutrophil precursors and include CFU-GEMM, CFU-GM, myeloblasts, promyelocytes and myelocytes. One reason for this is that these cells are understood to retain their capacity to proliferate, whereas more mature neutrophils, namely the metamyelocytes, band neutrophils and segmented neutrophils, are post-mitotic cells and have lost their proliferative capacity. The guiding principle has been that these progenitors and precursors would differentiate while in circulation as well as engraft into the neutrophil compartment and begin to produce neutrophils, and hence the time period of neutropenia would be reduced. There are several disadvantages to this strategy; one is that the transfusion of mitotic progenitor and precursor cells may require tissue matching, to minimise the risk of graft-versus-host disease (GVHD). Another is that the most efficient stem cell expansion techniques reported only produce a 150-250 fold increase of the initial starting material, which makes these processes expensive, and lastly, that progenitors do not offer the needed immediate protection of mature, segmented neutrophils. Because of the disadvantages, these therapies tend to be expensive and still leave a patient at risk of infection for a significant period of time.

Another therapy, neutrophil transfusion, is currently a treatment option that is reserved only as a last option for the critically ill. This is due to a number of factors including the number of doses, the neutrophils needed per dose, the difficulty involved in recruiting matched donors, and the need to submit the donors to a mobilisation and aphaeresis procedure.

Currently neutrophils are collected from donors through an aphaeresis procedure with or without mobilisation. Mobilisation involves pre-treating the donor at least 12 hours in advance with steroids such as dexamethesone as well as granulocyte colony stimulating factor (G-CSF), a growth factor specific for neutrophils. Without mobilisation a donor is subjected to a 2-4 hour aphaeresis procedure that yields an average of $20 \times 10^9$ neutrophils. With mobilisation the same aphaeresis procedure yield is typically increased to $60\text{-}80 \times 10^9$ neutrophils and each collection constitutes a single dose.

It is not known how many of the collected neutrophils are viable and un-activated, but based on clinical reports it is suspected that greater than 70% provide no therapeutic value, most likely due to activation. Additionally, because the aphaeresis procedure does not completely filter out other blood and immune cells, the donation must be a blood type match to the recipient and there is an increased risk of alloimmunization as a result.

A possible alternative to collecting neutrophils from donors could be to produce neutrophils ex vivo. However, as mentioned above, the focus to date has been on producing mitotic precursors or progenitors for expansion in vivo. Further, existing techniques for producing mature neutrophils ex vivo by expansion of stem cells such as described in PCT application WO 03/080806 not only include contact with stromal cells, which can lead to contamination and problems for regulatory approval, but they are inadequate for providing the numbers of non-activated cells needed for clinical purposes. Cultures in vessels such as T flasks cannot be readily scaled up for production of clinical quantities of cells needed to treat neutropenia, whereas the use of larger scale methods such as bioreactors has not resulted in adequate levels of expansion of functional cells.

Accordingly there is a need for an improved ex vivo method for producing mature neutrophils in sufficient quantities to make possible the use of ex vivo expanded mature neutrophils on a clinical scale in therapies based on the transfusion of mature neutrophils into neutropenic individuals or those deemed at risk of developing neutropenia.

SUMMARY OF THE INVENTION

It has now been found that the early stages of expansion in cell culture of haematopoietic stem cells and other progenitors are very sensitive to oxidative stress. The reason for this seems to be related to cell density and the ratio to reactive oxygen species. Progenitor cells, e.g. CD34+ cells, are typically seeded at a low initial density, e.g. from about 1,000 to 10,000 cells per ml. At this density, the cells appear to be particularly sensitive to reactive oxygen species, which results in poor cell expansion and cell death. However, we have found that after a period of time and once the cells have reached a certain density, they can be cultured under the more vigorous conditions that exist in large scale cultures to provide high yields of mature neutrophils. For example, it has been possible using the methods described herein to obtain a 5,000 to 10,000-fold expansion of progenitor cells to mature neutrophils.

Accordingly, in a first aspect the present invention provides an in vitro or ex vivo method of producing a population of post-mitotic cells of the neutrophil lineage, which method comprises the steps of:

(a) providing a population of cells comprising neutrophil progenitor cells; and (b) culturing the population of cells in an animal cell culture medium comprising (i) one or more early acting cytokines and (ii) one or more cytokines that differentiate said progenitor cells or progeny thereof into a neutrophil specific lineage, under conditions of low oxidative stress, the culture medium being agitated when the cells are at a cell density at which oxygen transfer via the surface of the culture medium is insufficient for growth of the progenitor cells and/or the progeny thereof under static conditions, to produce a population of post-mitotic cells of the neutrophil lineage.

In a related aspect, the present invention provides an in vitro or ex vivo method of producing a population of post-mitotic cells of the neutrophil lineage, which method comprises the steps of:

(a) providing a population of cells comprising neutrophil progenitor cells; and (b) culturing the population of cells in an animal cell culture medium comprising (i) one or more early acting cytokines and (ii) one or more cytokines that differentiate said progenitor cells or progeny thereof into a neutrophil specific lineage, under static conditions until the cells are at a cell density at which oxygen transfer via the surface of the culture medium is insufficient for growth of the progenitor cells and/or the progeny thereof under static conditions, and then agitating the culture medium thereafter, to produce a population of post-mitotic cells of the neutrophil lineage.

In a second aspect, the present invention provides an in vitro or ex vivo method of producing a population of post-mitotic cells of the neutrophil lineage, which method comprises the steps of:

(a) providing a population of cells comprising neutrophil progenitor cells;

(b) culturing the population of cells in an animal cell culture medium comprising (i) one or more early acting cytokines and (ii) one or more cytokines that differentiate said progenitor cells or progeny thereof into a neutrophil specific lineage, wherein the cells are cultured under conditions of low oxidative stress when the total cell density is less than from about 100,000 to about 200,000 cells per ml; and (c) agitating the medium once the total cell density is at least about 100,000 to about 200,000 cells per ml, to produce a population of post-mitotic cells of the neutrophil lineage.

In a related aspect, the present invention provides an in vitro or ex vivo method of producing a population of post-mitotic cells of the neutrophil lineage, which method comprises:

(a) providing a population of cells comprising neutrophil progenitor cells;

(b) culturing the population of cells in an animal cell culture medium comprising (i) one or more early acting cytokines and (ii) one or more cytokines that differentiate said progenitor cells or progeny thereof into a neutrophil specific lineage, wherein the cells are cultured under static conditions when the total cell density is less than from about 100,000 to about 200,000 cells per ml, the medium being agitated once the total cell density is at least about 100,000 to about 200,000 cells per ml; and (c) agitating the medium once the total cell density is at least about 100,000 to about 200,000 cells per ml, to produce a population of post-mitotic cells of the neutrophil lineage.

In a third aspect, the present invention also provides an in vitro or ex vivo method of producing a population of post-mitotic cells of the neutrophil lineage, which method comprises the steps of:

(a) providing a population of neutrophil progenitor cells;
(b) culturing the progenitor cells at an initial cell density of less than about 20,000 neutrophil progenitor cells per ml in an animal cell culture medium comprising (i) one or more early acting cytokines and (ii) one or more cytokines that differentiate progenitor cells or progeny thereof into a neutrophil specific lineage, under conditions of low oxidative stress, to produce a population of progeny cells at a density of at least about 100,000 cells per ml of medium; and
(c) culturing the population of progeny cells obtained in step (b) in an animal cell culture medium comprising (i) one or more early acting cytokines and (ii) one or more cytokines that differentiate said progeny cells into a neutrophil specific lineage, the medium being agitated, to produce a population of post-mitotic cells of the neutrophil lineage.

In one embodiment the initial culture medium further comprises cells other than neutrophil progenitor cells such that the total initial cell density is at least about 100,000 cells per ml of medium.

In a related aspect, the present invention also provides an in vitro or ex vivo method of producing a population of post-mitotic cells of the neutrophil lineage, which method comprises the steps of:

(a) providing a population of neutrophil progenitor cells;
(b) culturing the progenitor cells at an initial cell density of less than about 20,000 neutrophil progenitor cells per ml in an animal cell culture medium comprising (i) one or more early acting cytokines and (ii) one or more cytokines that differentiate said progenitor cells or progeny thereof into a neutrophil specific lineage, under static conditions, to produce a population of progeny cells at a density of at least about 100,000 cells per ml of medium; and
(c) culturing the population of progeny cells obtained in step (b) in an animal cell culture medium comprising (i) one or more early acting cytokines and (ii) one or more cytokines that differentiate said progeny cells into a neutrophil specific lineage, the medium being agitated, to produce a population of post-mitotic cells of the neutrophil lineage.

In a fourth aspect, the present invention further provides an in vitro or ex vivo method of producing a population of post-mitotic cells of the neutrophil lineage, which method comprises the steps of:

(a) providing a population of cells comprising neutrophil progenitor cells;
(b) culturing the population of cells at a total initial cell density of at least about 100,000 cells per ml in an animal cell culture medium comprising (i) one or more early acting cytokines and (ii) one or more cytokines that differentiate said progenitor cells or progeny thereof into a neutrophil specific lineage, the medium being agitated, to produce a population of post-mitotic cells of the neutrophil lineage.

In one embodiment the initial cell density of neutrophil progenitor cells is less than about 20,000 cells per ml.

In an alternative embodiment the initial cell density of neutrophil progenitor cells is at least about 20,000 cells per ml.

The present invention also provides an isolated population of post-mitotic cells of the neutrophil lineage obtained or obtainable by the method of the invention.

Preferably at least about 70% of the cells in the population of cells are post-mitotic cells of the neutrophil lineage.

Preferably comprises at least about 40% of the cells in the population of cells are mature band and segmented neutrophils.

Preferably less than about 20% of the cells are activated.

In a related aspect, the present invention provides a pharmaceutical composition comprising a population of cells of the invention, together with a pharmaceutically acceptable carrier or diluent, wherein the population of cells comprises at least 1 billion cells.

The present invention further provides a pharmaceutical composition comprising at least 5 billion ex vivo expanded post-mitotic cells of the neutrophil lineage, together with a pharmaceutically acceptable carrier or diluent. Preferably less than about 30 or 20% of the cells are activated.

The present invention also provides a method of increasing the number of neutrophils in a patient, which method comprises administering to the patient a population of cells of the invention or a pharmaceutical composition of the invention.

In a related aspect, the present invention provides a composition comprising a population of cells of the invention for use in increasing the number of neutrophils in a patient. Also provided is the use of a composition comprising a population of cells of the invention in the manufacture of a medicament for use in increasing the number of neutrophils in a patient.

The methods of the invention can also be used to expand progenitor cell populations to provide for expanded populations of progenitor and/or precursor cells. In this case, cells are harvested earlier in the culture process before they have differentiated to become post-mitotic cells of the neutrophil lineage.

Accordingly, the present invention further provides an in vitro or ex vivo method of producing an expanded population of neutrophil progenitor and/or neutrophil precursor cells which method comprises the steps of:

(a) providing a population of cells comprising neutrophil progenitor cells, and
(b) culturing the population of cells in an animal cell culture medium comprising (i) one or more early acting cytokines and (ii) one or more cytokines that differentiate said progenitor cells or progeny thereof into a neutrophil specific lineage, under conditions of low oxidative stress, the culture medium being agitated when the cells are at a cell density at which oxygen transfer via the surface of the culture medium is insufficient for growth of the progenitor cells and/or the progeny thereof under static conditions, to produce an expanded population of neutrophil progenitor and/or neutrophil precursor cells.

In a related aspect, the present invention provides an in vitro or ex vivo method of to producing an expanded population of neutrophil progenitor and/or neutrophil precursor cells which method comprises the steps of:

(a) providing a population of cells comprising neutrophil progenitor cells; and
(b) culturing the population of cells in an animal cell culture medium comprising (i) one or more early acting cytokines and (ii) one or more cytokines that differentiate said progenitor cells or progeny thereof into a neutrophil specific lineage, under static conditions until the cells are at a cell density at which oxygen transfer via the surface of the culture medium is insufficient for growth of the progenitor cells and/or the progeny thereof under static conditions, and then agitating the culture medium thereafter, to produce an expanded population of neutrophil progenitor and/or neutrophil precursor cells.

In a further aspect, the present invention provides an in vitro or ex vivo method of producing an expanded population of neutrophil progenitor and/or neutrophil precursor cells, which method comprises the steps of:

(a) providing a population of cells comprising neutrophil progenitor cells;

(b) culturing the population of cells in an animal cell culture medium comprising (i) one or more early acting cytokines and (ii) one or more cytokines that differentiate said progenitor cells or progeny thereof into a neutrophil specific lineage, wherein the cells are cultured under conditions of low oxidative stress when the total cell density is less than from about 100,000 to 200,000 cells per ml; and (c) agitating the medium once the total cell density is at least about 100,000 to about 200,000 cells per ml, to produce an expanded population of neutrophil progenitor and/or committed neutrophil precursor cells.

In a related aspect, the present invention provides an in vitro or ex vivo method of producing an expanded population of neutrophil progenitor and/or neutrophil precursor cells, which method comprises:

(a) providing a population of cells comprising neutrophil progenitor cells;

(b) culturing the population of cells in an animal cell culture medium comprising (i) one or more early acting cytokines and (ii) one or more cytokines that differentiate said progenitor cells or progeny thereof into a neutrophil specific lineage, wherein the cells are cultured under static conditions when the total cell density is less than from about 100,000 to about 200,000 cells per ml, the medium being agitated once the total cell density is at least about 100,000 to about 200,000 cells per ml; and (c) agitating the medium once the total cell density is at least about 100,000 to about 200,000 cells per ml, to produce an expanded population of neutrophil progenitor and/or neutrophil precursor cells.

In another aspect, the present invention also provides an in vitro or ex vivo method of producing an expanded population of neutrophil progenitor and/or neutrophil precursor cells, which method comprises the steps of:

(a) providing a population of neutrophil progenitor cells;

(b) culturing the progenitor cells at an initial cell density of less than about 20,000 neutrophil progenitor cells per ml in an animal cell culture medium comprising (i) one or more early acting cytokines and (ii) one or more cytokines that differentiate progenitor cells or progeny thereof into a neutrophil specific lineage, under conditions of low oxidative stress, to produce a population of progeny cells at a density of at least about 100,000 cells per ml of medium; and (c) culturing the population of progeny cells obtained in step (b) in an animal cell culture medium comprising (i) one or more early acting cytokines and (ii) one or more cytokines that differentiate said progeny cells into a neutrophil specific lineage, the medium being agitated, to produce an expanded population of neutrophil progenitor and/or neutrophil precursor cells.

In a related aspect, the present invention also provides an in vitro or ex vivo method of producing an expanded population of neutrophil progenitor and/or neutrophil precursor cells, which method comprises the steps of:

(a) providing a population of neutrophil progenitor cells;

(b) culturing the progenitor cells at an initial cell density of less than about 20,000 neutrophil progenitor cells per ml in an animal cell culture medium comprising (i) one or more early acting cytokines and (ii) one or more cytokines that differentiate said progenitor cells or progeny thereof into a neutrophil specific lineage, under static conditions, to produce a population of progeny cells at a density of at least about 100,000 cells per ml of medium; and (c) culturing the population of progeny cells obtained in step (b) in an animal cell culture medium comprising (i) one or more early acting cytokines and (ii) one or more cytokines that differentiate said progeny cells into a neutrophil specific lineage, the medium being agitated, to produce an expanded population of neutrophil progenitor and/or neutrophil precursor cells.

In a further aspect, the present invention further provides an in vitro or ex vivo method of producing an expanded population of neutrophil progenitor and/or neutrophil precursor cells, which method comprises the steps of:

(a) providing a population of cells comprising neutrophil progenitor cells;

(b) culturing the population of cells at a total initial cell density of at least about 100,000 cells per ml in an animal cell culture medium comprising (i) one or more early acting cytokines and (ii) one or more cytokines that differentiate said progenitor cells or progeny thereof into a neutrophil specific lineage, the medium being agitated, to produce an expanded population of neutrophil progenitor and/or neutrophil precursor cells.

The present invention also provides an expanded population of neutrophil progenitor and/or neutrophil precursor cells obtained or obtainable by the method of the invention.

In a related aspect, the present invention provides a pharmaceutical composition comprising an expanded population of neutrophil progenitor and/or neutrophil precursor cells obtained or obtainable by the method of the invention wherein the population of cells comprises at least 1 billion neutrophil progenitor and/or neutrophil precursor cells.

The various features described herein in relation to the method of the invention for producing post-mitotic cells of the neutrophil lineage apply *mutatis mutandis* to the method of the invention for producing an expanded population of neutrophil is progenitor and/or neutrophil precursor cells.

DETAILED DESCRIPTION OF THE INVENTION

Unless defined otherwise, all technical and scientific terms used herein have the same meaning as commonly understood by one of ordinary skill in the art (e.g. in cell culture, chemistry and molecular biology).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, reference to numerical values, unless stated otherwise, is to be taken as meaning "about" that numerical value. The term "about" is used to indicate that a value includes the inherent variation of error for the device and the method being employed to determine the value, or the variation that exists among the study subjects.

The term "low oxidative stress" means that the level of oxidative stress per cell is sufficiently low to avoid causing significant progenitor cell death as a result of the inability of the progenitor cells to repair cellular damage caused by reactive oxygen species. Cell death can be assessed by standard techniques, such as trypan blue exclusion.

Neutrophils differentiate from haematopoietic stem cells through a series of intermediate cell types, which can be distinguished by their microscopic morphological appearance, including such characteristics as the size of their nuclei, cell size, nuclear/cytoplasmic ratio, presence/absence of granules, and staining characteristics (See *Atlas of Blood Cells: Function and Pathology*, second edition, Zucker-Franklin et al.)

The term "neutrophil progenitor cells" will be used to refer to stem cells which can give rise to neutrophils, and other cells derived from such stem cells which can give rise to neutrophils and which can form colonies. Initially, the multipotent stem cells give rise to committed myeloid "progenitor cells" that generate precursors for all myeloid cell lines. The first myeloid progenitor is designated CFU-GEMM for "colony forming unit—granulocyte, erythroid, macrophage and megakaryocyte". The CFU-GEMM progenitor, in turn, will give rise to a CFU-GM progenitor cell, which is otherwise known as a "colony forming unit—granulocyte macrophage". In all of these descriptive terms, "colony" generally refers to a cell that is capable of giving rise to more than 50 cells as measured in 14 day in vitro assays for clonal growth. These cells will divide at least six times.

The CFU-GM is a committed progenitor—it is committed to differentiation into granulocytes and macrophages only. It is neither capable of differentiating into other types of cells nor is it capable of dedifferentiating into earlier stage progenitor cells. The CFU-GM progenitor cell may then differentiate into a myeloblast. The time required for differentiation from a CFU-GEMM to a myeloblast is believed to be about 1-4 days. A myeloblast is the first of the series of cells that may be referred to as cells specific to the neutrophil lineage, as such cells, once allowed to fully develop (differentiate), can only form neutrophils, which it is believed, are only capable of undergoing fewer than six cell divisions and, therefore, do not form colonies in in vitro assays as described previously.

Cells of the neutrophil-specific lineage are myeloblasts, promyelocytes, myelocytes, metamyelocytes, band or banded neutrophils, and segmented neutrophils. These can be subdivided into "neutrophil precursor cells" which are defined herein as myeloblasts, promyelocytes and myelocytes; and "post-mitotic cells of the neutrophil lineage" (also referred to as "mature neutrophils") which are defined herein as metamyelocytes, band or banded neutrophils, and segmented neutrophils.

During this progressive, morphological differentiation from stem cells to mature neutrophils, changes in the surface antigens of these cells can be observed. For example, haematopoietic stem cells, CFU-GEMM and CFU-GM are typically CD34+. Haematopoietic cells that differentiate beyond the CFU-GM stage are no longer CD34+. Similar progressions of expression are observed for the cell-surface antigens CD33 and CD45RA. All functional neutrophil cells can be characterized as CD34−, CD16+, and CD49d−. Band and segmented neutrophils can be further characterized as CD35+, CD87+, CD16+, and CD64− (Terstappen et. al. Leukemia 4:657, 1990; Elghetany et. al. J Clin Lab Analysis 18:36, 2004; Elghetany, Blood Cells Mol Dis 28(2):260, 2002). It should be appreciated, however, that such transitions in cell surface antigen expression are gradual, rather than abrupt, wherein some cells of a particular precursor cell type may be positive and other cells of the same type may be negative for a particular cell-surface antigen. Furthermore, the determination that a particular cell type is positive or negative for a particular cell-surface antigen will depend, in part, upon the particular method used to make that determination. The characterization of cell differentiation by cell-surface antigen expression may be confirmed by other means of characterizing cell differentiation, such as cell morphology.

In addition to changes in morphology and cell-surface antigen expression, as neutrophil precursor cells differentiate, they lose their capacity to proliferate (divide). In general, the less mature neutrophil precursor cells, namely the myeloblasts, promyelocytes, and myelocytes, retain their ability to proliferate. However, the more mature neutrophils, namely the metamyelocytes and the banded neutrophils, lose their capacity to proliferate, although they continue to differentiate into mature, segmented neutrophils.

Once differentiation has progressed to the myeloblast stage, the myeloblasts undergo terminal differentiation into promyelocytes, which, in turn, differentiate into myelocytes over a course of about 4-6 days. Within another 5 days or so, myelocytes differentiate into metamyelocytes, which, in turn, differentiate into banded neutrophils. These banded neutrophils finally differentiate into mature, segmented neutrophils, which have a half-life of about 0.3 to 2 days An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

Sources of Neutrophil Progenitor Cells

Neutrophil progenitor cells, as discussed above, are cells that can grow and differentiate in the presence of the appropriate growth factors, e.g. granulocyte-colony stimulating factor (G-CSF) into cells of the neutrophil lineage, e.g. metamyelocytes, bands and mature neutrophils. Neutrophil progenitor cells include both stem cells and committed progenitor cells. Particular examples include haematopoietic stem cells such as CD34+ stem cells, myeloid progenitor cells (e.g. CFU-mix, CFU-GEMM) and granulocyte/macrophage progenitor cells (e.g. CFU-GM). Preferred progenitor cells are CD34+.

Suitable sources of neutrophil progenitor cells include embryonic stem cell-derived progenitor cells, umbilical cord blood, bone marrow and peripheral blood, e.g. mobilized peripheral blood, which may be subject to one or more purification steps to purify progenitor cells from other cellular and non-cellular components. In particular, umbilical cord blood, peripheral blood, e.g. mobilized peripheral blood, or other similar sources, may be subject to an initial purification step to separate mononuclear cells (MNCs) from other components e.g. by Ficoll density gradient centrifugation.

In one embodiment, the source of neutrophil progenitor cells, including purified populations of mononuclear cells, is not subjected to a selection step to increase the relative numbers of neutrophil progenitor cells in the cell population, for example a selection step based on cell surface markers, e.g. CD34-based selection. Such a source is herein termed "non-enriched". The method of the invention does not require purification of CD34+ cells from other cells and the omission of this step represents a significant cost saving in the overall process.

In an alternative embodiment, the source of neutrophil progenitor cells is subject to a selection step to increase the relative numbers of neutrophil progenitor cells in the cell population, for example a selection step based on cell surface markers, such as CD34-based selection. Such a source is herein termed "enriched". Methods for isolating particular cell types e.g. on the basis of cell surface markers are well known in the art (such as the Dynal CD34 Progenitor Cell Selection System (Dynal A.S., Oslo, Norway) or the Miltenyi system described in the examples). One suitable method is described in the examples. In one embodiment, enrichment is performed by selecting for neutrophil progenitor cells. In an alternative embodiment enrichment is effected by removing one or more types of non-progenitor cells.

Cell Expansion Methodology

The neutrophil progenitor cells are typically resuspended in a culture medium suitable for the growth of animal cells, especially haematopoietic cells, such as Stemline II Haematopoietic Stem Cell Expansion Medium (Sigma Aldrich) or Iscove's modified Dulbecco's medium (IMDM) supplemented with fetal calf serum.

The population of neutrophil progenitor cells are seeded into a culture vessel at the desired starting density. In one embodiment, the initial density of neutrophil progenitor cells is less than about 20,000 cells per ml of culture medium, for example less than about 15,000 or 12,500 cells per ml of culture medium.

In a particular embodiment the initial density of neutrophil progenitor cells is less than about 7,500 or 5,000 cells per ml of culture medium, such as from about 1,000 to 3,000 cells per ml of culture medium. Typically, the initial density of neutrophil progenitor cells is at least about 1,000 cells per ml of culture medium. Alternatively, the initial density of neutrophil progenitor cells may be at least about 5,000 cells per ml of culture medium, such as from about 7,500 to 15,000 cells per ml of medium.

In one embodiment, the neutrophil progenitor cells form at least about 50%, such as at least about 70, 80 or 90%, of the cells seeded initially into the culture medium.

In an alternative embodiment, the initial population of cells may include substantial numbers of cells other than neutrophil progenitor cells. These cells may already be present in the biological source of the neutrophil progenitor cells and/or may be added to increase the total initial cell density to greater than the values given above in relation to neutrophil progenitor cells. The total initial cell density may be greater than about 20,000 cells per ml, such as at least about 50,000 or 100,000 cells per ml, for example at least 200,000 or 500,000 cells per ml. In one embodiment the initial total cell density is from about 200,000 to 400,000 cells per ml. In another embodiment, for example where unselected MNCs are used as a source, the total initial cell density may be in the range of from 500,000 to 5 million cells per ml.

The remainder of the cells other than the neutrophil progenitor cells may derive from the original source of the neutrophil progenitor cells e.g. cord blood cells, peripheral blood cells, and/or may be derived from a separate source e.g. peripheral blood cells added to the cell culture to bulk out the total cell content.

The initial volume of culture medium is typically at least about 10 ml, such as at least about 20, 50 or 100 ml, depending on the numbers of neutrophil progenitor cells available and the desired starting density of neutrophil progenitor cells. The initial volume of culture medium is typically less than about 5 L, such as less than about 2 L but may be more where large numbers of neutrophil progenitor cells are available.

Alternatively expressed, the initial volume of the culture medium may be about 10% or less of the final volume when the mature neutrophils are harvested, for example about 7, 5 or 2% or less of the final volume. The fold increase in culture medium volume may therefore be from about 10 fold to 50 or 100 fold.

The total number of neutrophil progenitor cells seeded initially into the culture is preferably greater than about 50,000, more preferably greater than about 100,000 or 200,000 cells.

The culture medium is a culture medium suitable for the growth of animal cells, as described above, supplemented with the growth factors required for cell expansion into neutrophils. The method of the invention is based on the use of two types of growth factors. The first type is early acting cytokines. These cytokines are not neutrophil pathway specific but act on stem cells and progenitor cells to promote growth and expansion. Examples of known early acting cytokines include the c-kit ligand, stem cell factor (SCF) and Flt-3 ligand (FL), as well as interleukins 1 to 12 (in particular IL-1, IL-2, IL-3, IL-6, IL-9, IL-10 and IL-12), thrombopoietin (TPO) and tumour necrosis factor alpha (TNFα). These cytokines are generally commercially available from companies such as Stem Cell Technologies, Amgen, Chemicon or can, for example, be produced recombinantly using standard techniques, or by peptide synthesis. Reference to various cytokines herein includes functionally equivalent molecules such as peptide mimetics e.g. TPO peptide mimetics (Cwirla S E, et al. (1997) Peptide Agonist of the Thrombopoietin Receptor as Potent as the Natural Cytokine. *Science* 276: 1696-1699; see also WO95/18858 and U.S. Pat. No. 6,835, 809.

The second type of cytokines are capable of directing differentiation of cells into a neutrophil specific lineage i.e. myeloblasts, premyelocytes, myelocytes, metamyelocytes, bands and mature neutrophils. Such cytokines include G-CSF and GM-CSF, and thrombopoietin. Again, these cytokines are generally commercially available from companies such as Amgen or can, for example, be produced recombinantly using standard techniques, or by peptide synthesis.

The cytokines are present in the culture medium at an amount effective in to promoting progenitor cell expansion/differentiation of progenitor cells into neutrophils, as appropriate. The cytokines are typically added to the culture medium at a concentration of from about 1 to 200 ng/ml, such as from about 5 to 100 ng/ml.

The culture medium therefore comprises one or more early acting cytokines and one or more cytokines, such as G-CSF, which promote differentiation of progenitor cells into neutrophil specific lineage cells.

Preferably the one or more early acting cytokines include SCF.

In one embodiment, the culture medium comprises less than about 1 ng/ml of IL-3 and/or IL-6. Preferably IL-3 and/or IL-6 have not been added to the culture medium (excluding any that may be naturally present in added components such as serum and the cells themselves).

It is preferred that the culture medium comprises thrombopoietin (TPO) or a peptide mimetic thereof, preferably at least during the first stage of the culture process when the culturing takes place under conditions of low oxidative stress, as described below.

In a particular embodiment, the culture media contains SCF, G-CSF, TPO, and optionally Flt-3, and no other cytokines in an effective amount.

The culture vessel may be any form of container suitable for the culture of animal cells, especially haematopoietic cells. Preferably the container is suitable for suspension culture of cells. Since the volume of cell culture will typically increase substantially during the culture process, preferred culture vessels are capable of being used to culture cells in volumes of culture medium from about 100 ml to 100 L, such as from about 500 or 1000 ml to 100 L without the need to transfer cells into different culture vessels. Accordingly, preferred culture vessels have a volume of at least about 1 L, more preferably at least about 2 or 5 L, such as at least about 10 L. However, in some embodiments, two or more different sizes of culture vessel may be used, with cells being transferred to a larger size of vessel at the appropriate point in the expansion process.

In one embodiment, the culture vessel is disposable or single-use (non reusable).

In a particularly preferred embodiment, the cells are cultured in a collapsible culture vessel, such as a flexible bag. The requirement for collapsibility/flexibility is such that the vessel can be partially or fully inflated. The vessel is typically made of a flexible plastic such as low density polyethylene. A particularly suitable culture vessel is described in U.S. Pat. No. 6,190,913. The plastic bag culture vessels described in U.S. Pat. No. 6,190,913 are available from Wave Biotech, NJ (Cellbag®) for use with the Wave Bioreactor®, in sizes ranging from 0.1 to 5 L, to 100 to 500 L.

During the first stage of the process when the progenitor cells and their progeny are often at a density at which the cells are particularly sensitive to the effects of oxidative stress, a number of different techniques can be used to reduce the oxidative stress experienced by the progenitor cells and the progeny thereof on a per cell basis.

In one embodiment, the cells are cultured under static conditions, i.e. without agitation, shaking and the like.

In another embodiment, the net effect of oxidative stress per progenitor cell is reduced by increasing the total number of cells in the culture medium using other cells. In this embodiment the initial total cell density is preferably at least about 50,000 or 100,000 cells per ml, more preferably at least about 200,000 or 500,000 cells per ml. In one embodiment the initial total cell density is from about 200,000 to 400,000 cells per ml. In another embodiment, for example where unselected MNCs are used as a source, the total initial cell density may be in the range of from 500,000 to 5 million cells per ml.

The remainder of the cells other than the neutrophil progenitor cells may derive from the original source of the neutrophil progenitor cells e.g. cord blood cells, peripheral blood cells, and/or may be derived from a separate source e.g. peripheral blood cells added to the cell culture to bulk out the total cell content. These additional cells may also include neutrophil precursors and mature neutrophils. In one embodiment, the remainder of the cells are primarily non-progenitor cells e.g. at least about 70 or 80% of cells other than neutrophil progenitor cells are non-progenitor cells, such as terminally differentiated cells such as erythrocytes, macrophages, and lymphocytes.

In a further embodiment, the levels of oxidative stress are reduced by the addition of agents that neutralise reactive oxygen species, i.e. antioxidants and radical scavengers. Examples of such agents that are suitable for animal cell culture include glutathione, 2-mercaptoethanol and other thiol compounds, pyruvate, ascorbate, catalase, serum albumin, and Pluronic F68.

In another embodiment, the level of oxidative stress is reduced by controlling the oxygen tension in the culture. The normal oxygen tension—in absence of cell metabolism—is around 20% dissolved oxygen (DO) for air with 5% $CO_2$. Preferably the dissolved oxygen (DO) content is less than about 10%, such as less than about 5%. In a particular embodiment where the initial progenitor cell density is less than about 5,000 cells per ml and the total initial cell density is less than about 100,000 cells per ml, the DO content is preferably less than about 10%.

In embodiments where the cells are seeded at a relatively low total cell density and oxidative stress is reduced by methods other than by increasing the initial cell density with non-progenitor cells (e.g. by using static cultures), in a first stage the cells are cultured until the desired cell density of neutrophil progenitor cells and progeny thereof (i.e. cells derived from the progenitor cells by proliferation/differentiation) is reached. In one embodiment, this is considered to be the density at which oxygen transfer via the surface of the culture medium is insufficient for growth of the progenitor cells and/or the progeny thereof under static conditions, i.e. dissolved oxygen is a limiting factor for cell growth.

In another embodiment the cells are cultured until the cell density, typically the density of neutrophil progenitor cells and progeny thereof, is at least about 50,000 or 100,000 cells per ml, such as from about 100,000 to 400,000 cells per ml or from about 100,000 to 200,000 cells per ml. In another embodiment, the cells are cultured until the cell density is at least about 200,000 cells per ml, such as from about 200,000 to 400,000 cells per ml.

During this initial step, there may be no addition of fresh medium or alternatively, fresh medium may be added. However, where there is no addition of fresh medium, additional nutrients, particularly growth factors, may optionally be added. This initial expansion step typically takes at least about 4 or 5 days, such as from about 4 to 9 days or from about 7 to 9 days.

Once the population of progeny cells has reached the desired cell density, the cells can then be subject to the second step of the culture process. In this second step the progenitor cells have expanded sufficiently and reached a sufficient cell density that they can be cultured under the more vigorous conditions used in large scale cell culture methods. In embodiments where the initial total cell density is already sufficiently high, the first step is effectively omitted and agitation can be performed from the beginning of the culture process.

Agitation of the cells is used in this second step since under static conditions there would be insufficient transfer of oxygen into the culture medium to properly sustain the cells. Similarly, the mixing of nutrients within the culture medium is beneficial to the cells. Accordingly, agitation of the culture medium should commence no later than when the total cell density is such that static culture conditions would provide inadequate cell feeding and growth. This can be determined by a person skilled in the art by, for example, growing the cells under static conditions and observing the point at which the rate of cell growth starts to diminish.

The cells are subject to agitation, such as by stirring, e.g. in a stirred tank-type bioreactor, rolling, e.g. roller bottle cultures, or wave motion, e.g. in a collapsible culture vessel, such as the Cellbag described above, which is subject to rocking. Again, in one embodiment, the culture vessel is disposable or single-use (non reusable).

In more detail, the Cellbag is typically filled with liquid culture medium so that the culture medium comprises between about 10 to 50% of the volume of the bag. As a guide, the volume of liquid media will initially be smaller when dilution feeding is used (to allow room for an increase in culture volume) but can be greater where fresh culture feeding is achieved by perfusion methods or the like. The remainder of the bag is then generally filled with an oxygen-containing gas such that the bag becomes rigid. The bag is generally inflated to allow sufficient headspace between the surface of the culture medium and the top of the bag so that waves can form on the surface of the culture medium when the bag is gently rocked.

The bag is secured to a platform which is rocked in a single degree of freedom to thereby induce a wave motion to the liquid medium in the bag. The necessary oxygen transfer and mixing required for cell growth and productivity is accomplished by the wave motion. The rocking is typically carried out through an angle of from about 1 to 15 degrees from a horizontal position of the platform. The rate of rocking is typically from about 1 to 20 rocks per minute.

There are two main approaches to cell feeding. In one embodiment, the cells can be fed by the addition of fresh media, such that the volume of the culture medium increases during the second stage of the culture process. This is termed dilution feeding. Preferably, feeding is carried out at sufficient intervals to ensure that the total cell density is maintained at less than about 5 million cells per ml, e.g. less than about 4 or 2 million cells per ml of culture medium.

In an alternative embodiment, the volume of the culture medium is kept substantially constant and the cells fed by removal of old medium and replacement with fresh medium, but without removing substantial numbers of viable cells. One suitable method is termed perfusion (e.g. Koller et al., 1993, Blood 82: 378-384), which may be continuous or discontinuous.

In a further embodiment, the two techniques described above can be combined e.g. perfusion is used but the volume of the culture medium is increased over time by adding in more fresh medium than is removed to ensure that the cell density does not increase above a desired level.

It is generally preferred, whichever feeding method is used, to maintain the total number of cells at a minimum density of at least about 400,000 cells or 500,000 cells per ml during the second culture step.

In both stages of culture, the temperature of the culture medium is generally maintained at from about 35 to 39° C., preferably from about 36 to 38° C., such as about 37° C. The optimum $CO_2$ levels are generally from about 3 to 10% $CO_2$, such as from about 4 to 6% $CO_2$, preferably about 5% $CO_2$.

In this second stage, the one or more early cytokines may be different to the first stage, for example TPO may be omitted.

The cells are cultured for a sufficient time to allow for optimum expansion and production of post-mitotic cells of the neutrophil lineage. Typically the second stage takes from 5 to 15 days, such as from 5 to 7 days. The progress of expansion/differentiation can be monitored using standard techniques e.g. aliquots of cells can be taken at intervals and examined under the microscope, following Giemsa staining, to identify mature neutrophils, which have a characteristic morphology. Cells may also be analysed to determine the presence of mature neutrophil-specific cell surface markers such as CD16 using standard techniques such as fluorescence activated cell sorting (FACS).

Cells may also be tested to determine neutrophil activity. Functional tests include superoxide releasing capacity e.g. as determined by SOD-inhibitable reduction of ferricytochrome c (You et al., 1989, Blood 74: 2144-2149); chemotactic activity e.g. using the Boyden method (Boyden, 1962, J. Exp. Med. 115: 971-975) or the method described by Zigmond, 1988 (Methods Enzymol. 162: 65-72).

The total time from initial seeding of cells in the first stage until the cells are ready for harvesting is typically from about 12 to 18 days. Cells are preferably harvested after a minimum of about 12 days and a maximum of about 18 days.

It is preferred that harvesting of the cells takes place when at least about 70, 80 or 90% of the cells are post-mitotic cells of the neutrophil lineage.

Harvested cells are typically washed and resuspended in a medium suitable for therapeutic administration such as platelet storage solutions (e.g., Plasmalyte A or T-Sol—both available from Baxter Healthcare, Deerfield, Ill.).

The results shown herein demonstrate a 5000-fold expansion of neutrophil progenitor cells to post-mitotic neutrophils. Accordingly, it is preferred that the method of the invention results in at least about a 1000-fold expansion, more preferably about a 2000- or 4000-fold expansion of the population of progenitor cells to post-mitotic cells of the neutrophil lineage.

Preferably the total number of post-mitotic cells of the neutrophil lineage obtained is at least 500 million, such as at least 1 billion, more preferably at least 2, 5, 10, 15 or 20 billion. Preferably the final volume of the culture medium when the cells are harvested is at least about 10 L, such as at least about 20, 50 or 100 L Preferably, the population of post-mitotic cells has at least about 40 or 50% of the biological activity of a population of peripheral blood neutrophils having the same number of cells, more preferably about 70, 75, 80 or 90% of the activity of the population of peripheral blood neutrophils. Biological activity in this context is preferably measured as superoxide releasing capacity.

The methods described above may also be used to obtain an expanded population of neutrophil progenitor and/or neutrophil precursor cells. In this embodiment, the cells are harvested at an earlier stage before the majority of progenitor and precursor cells have differentiated to produce mature neutrophils. The cells are typically harvested at from about 10 to 12 days after the initial population of neutrophil progenitor cells were seeded into the culture medium.

Accordingly, the present invention also provides an in vitro or ex vivo method of producing an expanded population of neutrophil progenitor and/or neutrophil precursor cells, which method comprises the steps of:
(a) providing a population of cells comprising neutrophil progenitor cells; and
(b) culturing the population of cells in an animal cell culture medium comprising (i) one or more early acting cytokines and (ii) one or more cytokines required for expansion of said progenitor cells, under conditions of low oxidative stress, the culture medium being agitated when the cells are at a cell density at which oxygen transfer via the surface of the culture medium is insufficient for growth of the progenitor cells and the progeny thereof under static conditions,
to produce an expanded population of neutrophil progenitor and/or neutrophil precursor cells.

In a related aspect, the present invention provides an in vitro or ex vivo method of producing an expanded population of neutrophil progenitor and/or neutrophil precursor cells, which method comprises the steps of:
(a) providing a population of cells comprising neutrophil progenitor cells; and
(b) culturing the population of cells in an animal cell culture medium comprising (i) one or more early acting cytokines and (ii) one or more cytokines required for expansion of said progenitor cells, under static conditions until the cells are at a cell density at which oxygen transfer via the surface of the culture medium is insufficient for growth of the progenitor cells and/or the progeny thereof under static conditions, and then agitating the culture medium thereafter,
to produce an expanded population of neutrophil progenitor and/or neutrophil precursor cells.

The various embodiments, definitions, conditions and aspects described above in relation to the production of mature neutrophils apply *mutatis mutandis* to the production of expanded populations of neutrophil progenitor and/or neutrophil precursor cells, taking into account in particular that, as mentioned above, cells will be harvested at an earlier stage.

The present invention also provides a population of expanded populations of neutrophil progenitor and/or neutrophil precursor cells obtained or obtainable by the method of the invention.

Therapeutic Compositions and Uses Thereof

The method of the invention can be used to provide clinical quantities of post-mitotic cells of the neutrophil lineage for use in treating or avoiding disorders such as neutropenia or infection. Accordingly the present invention provides a pharmaceutical composition comprising an isolated population of cells comprising at least about 1 billion post-mitotic cells of the neutrophil lineage, more preferably at least about 2, 5, 10, 15 or 20 billion post-mitotic cells of the neutrophil lineage, together with a pharmaceutically acceptable carrier or diluent. Typically, the cells have been produced by the method of the invention.

Preferably at least about 60%, 70%, 80% or 90%, more preferably at least about 95%, of the cells in the composition are post-mitotic cells of the neutrophil lineage.

Preferably at least about 40%, more preferably at least about 50, 60, 70 or 80% of the cells are mature neutrophils.

Since activated neutrophils are not useful clinically, typically less than about 30 or 20% of the neutrophils are activated.

Preferably, a population of post-mitotic cells of the neutrophil lineage according to the present invention has at least about 40% or 50% of the biological activity of a population of peripheral blood neutrophils having the same number of cells, more preferably at least about 70, 75, 80 or 90% of the activity of the population of peripheral blood neutrophils. Biological activity in this context is preferably measured as superoxide releasing capacity.

The populations of post-mitotic neutrophil cells of the present invention and compositions comprising the same can be used to treat patients in need of increased levels of neutrophils or that could benefit from increased levels of neutrophils, such as to treat a condition associated with a transient or permanent decrease in the number or functionality of neutrophils (e.g. neutropenia, leukaemia).

Normal patients typically have a neutrophil count of $2.5 \times 10^9$ to $7.5 \times 10^9$ cells per litre of blood, which is equivalent to an absolute neutrophil count (ANC) of 2500 to 7500 cells per microlitre of blood. Neutropenia is classed as ANC<2000, mild neutropenia: 1000<ANC<1500; moderate neutropenia: 500<ANC<1000; severe neutropenia: ANC<500. Increased levels of neutrophils in relation to achieving a therapeutic effect are therefore preferably an increase in ANC of at least about 100 or 500, more preferably at least about 1000 or 2000. An "effective amount" is accordingly the dose of cells required to achieve such an increase. The compositions of the invention can be administered to a patient by any suitable mode. The preferred routes of administration will be apparent to those of skill in the art, depending on the type of condition to be prevented or treated. Preferred methods of administration include, but are not limited to, intravenous, intraperitoneal, intracoronary, intraarterial, intraarticular, and intraventricular administration, impregnation of a catheter, and direct injection into a tissue.

Neutrophils can be administered with pharmaceutically acceptable carriers or diluents. Examples include, but are not limited to water, saline, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

According to the present invention, an effective administration protocol comprises suitable dose parameters and modes of administration that result in delivery of a useful number of functional neutrophils to a patient to provide a transient or long term benefit to the patient. Effective dose parameters can be determined using methods standard in the art for a particular condition or disease. Such methods include, for example, determination of survival rates, side effects (i.e. toxicity) and progression or regression of disease.

A suitable single dose of neutrophils according to the present invention is a dose that is capable of providing a beneficial number of neutrophils to a patient, when administered one or more times over a suitable time period. For example, a preferred single dose of neutrophils according to the present invention is from about $1 \times 10^8$ to about $5 \times 10^{10}$ neutrophils per individual per administration, such as from about $1 \times 10^9$ to about $5 \times 10^{10}$. It will be apparent to one of skill in the art that the number of doses administered to a patient is dependent upon the extent of the condition or disease and the response of an individual patient to the treatment.

Treatment may include reducing the symptoms of the disease; reducing the occurrence of the disease, and/or reducing the severity of the disease. As such, treatment includes both preventing disease occurrence (prophylactic treatment) and treating an animal that has a disease or that is experiencing initial symptoms of a disease (therapeutic treatment). The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

In the method of the present invention, population of cells according to the present invention and composition comprising the same can be administered to any animal or human, e.g. mammals such as primates, rodents, livestock and domestic pets.

The present invention will now be described further with reference to the following examples which are illustrative only and non-limiting.

EXAMPLES

Materials and Methods

Cord Blood Collection

Human Umbilical Cord Blood (UCB) samples from full term deliveries were obtained with informed consent of the mothers from the Royal Brisbane Hospital (Brisbane, Australia). Approximately 30 to 50 ml cord blood was routinely recovered and collected in 50 ml tubes containing 250 IU sodium heparin (DBL). Cord Blood Samples were stored at ambient temperature and processed within 24 hours of collection.

CD34+ Cell Selection

Mononuclear cells (MNC) were separated by density gradient centrifugation over Ficoll-Paque Plus (Amersham) and enriched in CD34+ cells by two rounds of positive selection using the Midi and Mini-MACS columns and Direct CD34+ Progenitor Cell Isolation Kit (Miltenyi Biotech) following the manufacturer's recommendations.

Briefly, cord blood was diluted (1:4) in calcium and magnesium free phosphate-buffered-saline (PBS) containing 2 mM EDTA, layered on a Ficoll-Paque Plus density gradient and centrifuged at 450 g for 30 minutes at ambient temperature to separate the mononuclear cells. The buffy coat was collected, washed and contaminating red blood cells (RBC) removed by ammonium chloride lysis.

Following lysis, cells were washed and resuspended in MACS buffer (PBS+2 mM EDTA+0.5% bovine serum albumin (BSA). The cells were then incubated firstly with the FcR blocking reagent and secondly with the MACS paramagnetic MicroBeads coated with CD34 antibodies from the isolation kit. After the incubation step the cells were washed and passed through a pre-separation filter before being applied to a pre-equilibrated positive selection column (LS+) held in a magnetic field. The column was washed three times with MACS buffer during which time the non-binding unlabelled cells passed through the column while the CD34+ cells were retained within the column. CD34+ cells were recovered by releasing the magnetic field and flushing cells from the column. The eluted cells were washed in MACS buffer and the magnetic separation step was then repeated with cells applied to a second pre-filled positive selection column (MS+). CD34+ cells were used immediately after separation. The typical purity of the CD34+ cells was >90%. Following selection, the CD34+ cells were resuspended in 1 ml Stemline II Haematopoietic Stem Cell Expansion Medium (Sigma Aldrich).

Cytokines

Stem cell factor (rhSCF) and granulocyte colony stimulating factor (rhG-CSF) were obtained from Amgen. Recombinant human thrombopoietin (rhTPO) was obtained from Chemicon. TPO peptide mimetic was obtained from Auspep.

Example 1

Ex Vivo Expansion of Neutrophil Progenitor Cells—Effect of Cell Density and Agitation Following purification and selection as described above, CD34+ cells from umbilical cord blood were resuspended in 1 ml Stemline II Haematopoietic Stem Cell Expansion Medium (Sigma Aldrich) and seeded into T-flasks at a density of either 2,000 cells per ml or 10,000 cells per ml.

Cells were seeded in Neutrophil Complete Media (Stemline II supplemented with stem cell factor (rhSCF) 100 ng/ml, granulocyte colony stimulating factor (rhGCSF) 100 ng/ml and 100 ng/ml TPO peptide mimetic.

Cells were incubated for 12 days in an incubator at 37° C., 5% $CO_2$, either with rocking (15 rocks/min, 8° angle) or without rocking (static).

The results obtained showed that rocking reduced expansion by 20- to 50-fold. Rocking therefore had a significant, adverse impact on the levels of expansion of neutrophils from progenitor cells, although the effect was less severe with cells seeded at the higher density.

The experiment was repeated but with the cells being cultured under static conditions for 9 days followed by rocking from day 9 onwards. The results showed that there was no difference in the levels of expansion between cultures that were static for the entire course of the experiment and those that were rocked after day 9. From measurements of cell density, we conclude that the deleterious effects of agitation can be avoided if cells are allowed to reach a minimum cell density e.g. at least about 100,000 to 200,000 cells per ml, prior to agitation.

Example 2

Effect of Dissolved Oxygen (DO) Levels on Vivo Expansion of Neutrophil Progenitor Cells Following purification and selection as described above, CD34+ cells from umbilical cord blood were resuspended in 1 ml Stemline II Haematopoietic Stem Cell Expansion Medium (Sigma Aldrich) and seeded in Neutrophil Complete Media into T-flasks at a density of either 2,000 cells per ml or 10,000 cells per ml.

Cells were incubated under conditions of either low dissolved oxygen (5%) or high dissolved oxygen (20%). At the lower cell density of 2,000 cells per ml, the levels of expansion seen were significantly lower with high DO versus low DO. However, no significant difference was seen when cells were seeded at the higher cell density. We suggest that this is due to the effects of oxidative stress on the cells, these effects being proportionately greater for a given level of DO when lower numbers of cells are used initially.

There are several approaches that could be used to reduce the levels of oxidative stress experienced by the cells. Firstly, the initial cell density could be increased. Since it is preferred not to seed the progenitor cells themselves at high density, one way to achieve higher cell density without the need for using larger numbers of progenitor cells is to bulk the progenitor cells out with non-progenitor cells, such as peripheral blood cells. Another approach is to culture the cells under static conditions until the density of progeny cells reaches the desired minimum cell density prior to commencing agitation—as demonstrated in Example 4. A further possibility is to adjust the media formulation to include ingredients that scavenge oxygen radicals and/or to regulate the oxygen tension.

Example 3

Comparison of rhTPO with TPO Peptide Mimetic

Following purification and selection as described above, CD34+ cells from umbilical cord blood were resuspended in 1 ml Stemline II Haematopoietic Stem Cell Expansion Medium (Sigma Aldrich) and seeded into T-flasks at a density of 2,000 cells per ml.

Cells were seeded in Neutrophil Complete Media. The source of TPO was either recombinant human thrombopoietin at 100 ng/ml, or TPO peptide mimetic at 4, 20 or 100 ng/ml.

Cells were incubated for 12 days in an incubator at 37° C., 5% $CO_2$ under static conditions Similar results were obtained with rhTPO, 20 ng/ml TPO peptide and 100 ng/ml TPO peptide mimetic, demonstrating that TPO peptide is as potent as rhTPO.

Since TPO peptide mimetic is significantly cheaper than rhTPOs, the use of the TPO peptide is advantageous in terms of cost.

Example 4

Ex Vivo Expansion of Neutrophil Progenitor Cells in CellBags

Materials and Methods

Following purification and selection as described above, CD34+ cells from umbilical cord blood were resuspended in 1 ml Stemline II Haematopoietic Stem Cell Expansion Medium (Sigma Aldrich). Cells were counted using a haemocytometer and cultured ex vivo for up to 17 days in a 2 L FEP CellBag as part of the Wave Bioreactor System (Wave Biotech) as described below.

Cells were seeded at 200,000 cells/20 ml total volume in Neutrophil Complete Media (TPO source was TPO peptide mimetic at 100 ng/ml).

Cells were applied to the cellbag at 2× the seeding density in 10 ml neutrophil complete media via a luer lock sample port on the bag and this was followed by 10 mL fresh media to wash the cells from the tubing taking the density and volume to the appropriate level. The cellbag was not inflated at this point and was placed in the incubator at 37° C., 5% $CO_2$ in a fully humidified atmosphere and left static and untouched until Day 5 of culture. In parallel 10 ml of the same 2× density cell suspension was added to the flask along with 10 ml fresh media and was incubated under the same conditions, not touched until Day 5.

At Day 5, the medium in the cellbag was diluted by adding an equal volume of fresh medium (half-dilution), i.e. 20 ml.

At Day 7, the medium in the cellbag was diluted by adding an equal volume of fresh medium (half-dilution), i.e. 40 ml.

At Day 9 and every other day thereafter (11, 13, 15), the cellbag was diluted back to about 500,000 cells/ml with fresh medium. Moreover, the cellbag was inflated by continuous aeration (0.1 L/min) and the cultures gently rocked (5 rocks/min, 7° angle) for the remainder of the culture period.

Samples for analysis were withdrawn every other day starting from day 5 from both vessels after a thorough mixing of the cultures. Cells were counted using a haemocytometer to determine cell density and viability. Cell viability was assessed microscopically using trypan blue to distinguish viable from non-viable cells.

Cytospin preparations of cultured cells were prepared on days 13, 15 and/or days that coincided with functional testing using a cytocentrifuge attachment for a Sigma centrifuge with $1 \times 10^5$ cells per slide. The slides were fixed with Leishman's stock for 2 mins and stained for 8 mins in a 1:6 dilution of Leishman's stock in pH 6.8 phosphate buffer. The slides were then evaluated for the presence of myeloblasts, promyelocytes, myelocytes, bands and segmented neutrophils. The presence of mitotic, apoptotic and other cell populations was also noted.

Results

At day 16, the final culture volume was about 1000 ml with a cell density of about 1,000,000 cells per ml following the final dilution, giving a total of 1000 million cells in a volume of 1000 ml. Since the initial culture containing 200,000 cells in 20 ml, the fold increase in expansion as determined by cells final/cells initial was about 5000-fold. This is a significantly greater degree of expansion than has been obtained previously using other techniques.

The population of expanded cells were also tested for neutrophil function. The results obtained indicated that the neutrophils were not activated (i.e. were safe to infuse) but had the ability to become activated in the presence of appropriate stimuli. They had superoxide function (ability to kill bacteria) at the lower limit of normal when compared with normal peripheral blood neutrophils. In addition, cells farmed at days 13, 16 and 18 exhibited chemotaxis in response to a stimulus which mimicked their ability in vivo to migrate to a focus of bacterial infection.

The cells also appeared to express normal levels of HLA Class I antigens and neutrophil specific antigens, indicating that they are fully mature cells. An automated 5 part machine differential count on the day 16 and day 18 cultures demonstrated that 80% of cells were mature neutrophils. This was confirmed by manual differential counts of a total of 200 cells on Giemsa stained smears.

Accordingly, not only was significant cell expansion obtained, but the resulting cells were both at a mature, post-mitotic stage and functional.

For comparison, a control experiment was run using a low density polypropylene Cellbag or Teflon cellbag where the cells were agitated and headspace aeration used for the entire duration of the experiment. This reflects the typical conditions used in a bioreactor scale-up. The results obtained in the control experiment showed poor levels of expansion, in the region of 100-fold. It can therefore be seen that the method of the invention results in significantly better expansion of neutrophil cells, when scaled up to volumes of over a litre than existing bioreactor-based cell culture and expansion methodologies.

Example 5

Expansion of Non-Enriched Sources of Progenitor Cells

The methodology described in Example 4 was repeated with the exception that the mononuclear cells obtained after purification of cord blood on a Ficoll-Paque Plus density gradient were used directly with no CD34+ enrichment step. Cells were seeded at an initial density of 2000 CD34+ cells per ml in 15 to 20 ml of culture medium. The total cell density depended on the particular cord used (range 150,000 to 500,000 cells per ml), the remainder of the cells being other types of blood cells).

The results obtained with non-enriched cell populations were significantly better than those obtained with cell populations enriched for CD34+ cells (10,000-fold, non-selected, at day 15 versus 6,000-fold at day 15, selected).

The various features and embodiments of the present invention, referred to in individual sections above apply, as appropriate, to other sections, *mutatis mutandis*. Consequently features specified in one section may be combined with features specified in other sections, as appropriate.

All publications mentioned in the above specification are herein incorporated by reference. All of the compositions and/or methods disclosed and claimed in this specification can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. An in vitro or ex vivo method of producing a population of post-mitotic cells of the neutrophil lineage, which method comprises the steps of:
   (a) providing a population of cells comprising neutrophil progenitor cells in an animal cell culture medium and at an initial cell density;

(b) culturing the population of cells under conditions of low oxidative stress, wherein the animal cell culture medium comprises (i) one or more early acting cytokines and (ii) one or more cytokines that differentiate said progenitor cells into a neutrophil specific lineage;

(c) determining a cell density at which the culture is thereafter to be agitated; and (d) agitating the culture medium during continued culture of the cells once the cells reach the cell density determined in (c) to produce at least a 1000-fold expansion of the population of progenitor cells to post-mitotic cells of the neutrophil lineage.

2. The method of claim 1, wherein the conditions of low oxidative stress of step (b) comprise a dissolved oxygen content of the culture less than about 10%.

3. The method of claim 1, wherein the culturing of the population of cells of step (b) comprises culturing the population in static conditions.

4. The method of claim 1, wherein the initial cell density of neutrophil progenitor cells is less than about 20,000 cells per ml.

5. The method of claim 4, wherein the culture medium of step (a) further comprises cells other than neutrophil progenitor cells such that the total initial cell density is at least about 100,000 cells per ml of medium.

6. The method of claim 5, wherein the cells other than neutrophil progenitor cells are mononuclear cells derived from blood.

7. The method of claim 1, wherein the cell density of step (c) is that cell density at which the rate of cell growth of the progenitor cells and the progeny thereof starts to diminish as a result of insufficient oxygen transfer via the surface of the culture medium under static conditions.

8. The method of claim 1, wherein the cell density of step (c) is at least about 100,000 to about 200,000 cells per ml.

9. The method of claim 1, wherein the cell density of step (c) is the initial cell density of step (b).

10. The method of claim 1, wherein the population of neutrophil progenitor cells has been enriched.

11. The method of claim 1, wherein the population of neutrophil progenitor cells is provided as a non-enriched population of mononuclear cells.

12. An in vitro or ex vivo method of producing an expanded population of neutrophil progenitor and/or neutrophil precursor cells, which method comprises the steps of:

(a) providing a population of cells comprising neutrophil progenitor cells; and (b) culturing the population of cells in an animal cell culture medium comprising (i) one or more early acting cytokines and (ii) one or more cytokines required for expansion of said progenitor cells, under static conditions until the cells are at a cell density at which the rate of cell growth of the progenitor cells and the progeny thereof starts to diminish as a result of insufficient oxygen transfer via the surface of the culture medium under static conditions, and then agitating the culture medium thereafter, to produce at least a 1000-fold expansion of the population of neutrophil progenitor and/or neutrophil precursor cells.

* * * * *